United States Patent [19]

Snyder

[11] Patent Number: 5,052,806

[45] Date of Patent: Oct. 1, 1991

[54] APPARATUS FOR MEASURING NON-ABSORPTIVE SCATTERING

[75] Inventor: James J. Snyder, San Jose, Calif.

[73] Assignee: Blue Sky Research, Inc., San Jose, Calif.

[21] Appl. No.: 527,016

[22] Filed: May 21, 1990

[51] Int. Cl.$^5$ .................... G01N 21/49; G01B 9/02
[52] U.S. Cl. .................... 356/343; 356/349; 356/441
[58] Field of Search ........... 356/349, 338, 343, 432, 356/438, 441; 250/574

[56] References Cited

U.S. PATENT DOCUMENTS 4,397,550  8/1983  Matsuda et al. .................. 356/349

Primary Examiner—Richard A. Rosenberger
Attorney, Agent, or Firm—Joseph H. Smith

[57] ABSTRACT

Apparatus is provided for measuring non-absorptive scattering with an exceptionally high degree of accuracy. In the preferred mode, the apparatus can also be used to measure absorptive scattering, thus providing a method of distinguishing absorptive scattering from scattering due to transparent moieties (i.e. non-absorptive scattering). The approach of the invention promises to significantly expand the use of optical systems in quality control. The general concept of the invention relies on symmetric heterodyne scattering. Specifically, two beams at slightly differing optical frequencies are directed to intersect at some arbitrary angle. Transparent objects within the intersection volume scatter light from each beam into the other. After intersecting, the two beams are directed to separate photodetectors which mix each transmitted beam with the scattered light from the other beam. Because the two beams are at different optical frequencies, the mixing of the light generates heterodyne (beat) signals modulated at the difference frequency on each of the photodetectors. These signals can then be combined in various ways to directly measure the absorptive and non-absorbtive scattering from the scattering region.

7 Claims, 5 Drawing Sheets

APPARATUS FOR MEASURING NON-ABSORPTIVE SCATTERING

FIELD OF THE INVENTION

This invention relates to the use of twin photon beams for symmetric hetereodyne scattering which can be used to distinguish non-absorptive scattering from absorption.

BACKGROUND OF THE INVENTION

An important aspect of optical measurments which has long been difficult to perform is to distinguish scattering from absorbing particles from scattering from non-absorbing (or transparent) scatterers. Such measurements can be exceedingly important in industries where it is necessary to distinguish particulates from bubbles for example. Hence, such measurements can be vital to quality control.

What is needed is a new and accurate method for quantitatively distinguishing absorbtive scattering from non-absorbtive scattering.

SUMMARY OF THE INVENTION

In accordance with preferred embodiments of the invention, an apparatus is provided for measuring non-absorptive scattering with an exceptionally high degree of accuracy. In the preferred mode, the apparatus can also be used to measure absorptive scattering, thus providing a method of distinguishing absorptive scattering from scattering due to transparent moieties (i.e. non-absorptive scattering). The approach of the invention promises to significantly expand the use of optical systems in quality control.

The general concept of the invention relies on symmetric heterodyne scattering. Specifically, two beams at slightly differing optical frequencies are directed to intersect at some arbitrary angle. Transparent objects within the intersection volume scatter light from each beam into the other. After intersecting, the two beams are directed to separate photodetectors which mix each transmitted beam with the scattered light from the other beam. Because the two beams are at different optical frequencies, the mixing of the light generates heretodyne (beat) signals modulated at the difference frequency on each of the photodetectors. These signals can then be combined in various ways to directly measure the absorptive and non-absorbtive scattering from the scattering region.

More specifically, according to a preferred embodiment of the invention, an apparatus is provided for measuring non-absorptive scattering from a scattering region. The apparatus includes a source for producing two laser beams having equal optical powers, with one of the beams being shifted in frequency relative to the other, the two beams oriented to cross in the scattering region. Also included is a detector system for independently detecting each of the two beams after they have traversed the scattering region, the detector means providing first and second signals, one for each of said two beams. A differencing element then provides a difference signal proportional to the difference between the first and second signals from the detector system, the difference signal corresponding to the anti-correlated portions of the first and second signals from the detector system.

In a preferred mode, the source includes a laser for providing a laser beam, a splitter for splitting the laser beam into the two beams, a shifter for shifting the frequency of one of the two beams relative to the other, and a mirror element for directing the two beams to cross in the scattering region. Also in a preferred ode, the detector system has first and second separate photodetectors, one for each of the two beams, with the first photodetectors providing the first signal and the second photodetector providing the second signal. Also in a preferred mode, the differencing element includes a first amplifier for amplifying the first signal, a first splitter for splitting the first amplified signal into two equal first splitter signals, a second amplifier for amplifying the second signal, a second splitter for splitting the second amplified signal into two equal second splitter signals, and a combined means for subtracting one of the first splitter signals from one of the second splitter signals. A second in-phase combiner can then be used to sum the other signal from the first and second splitters to provide a signal proportional to the absorptive scattering, i.e. to the correlated portions of the first and second signals.

FIG. Symmetric heterodyne scattering. An object with transmission $\tau$ located in the intersection volume of two beams of different optical frequencies scatters some of the light of each beam into the other beam. Two photodetectors produce difference frequency heterodyne signals which are added or subtracted.

Figure 3:
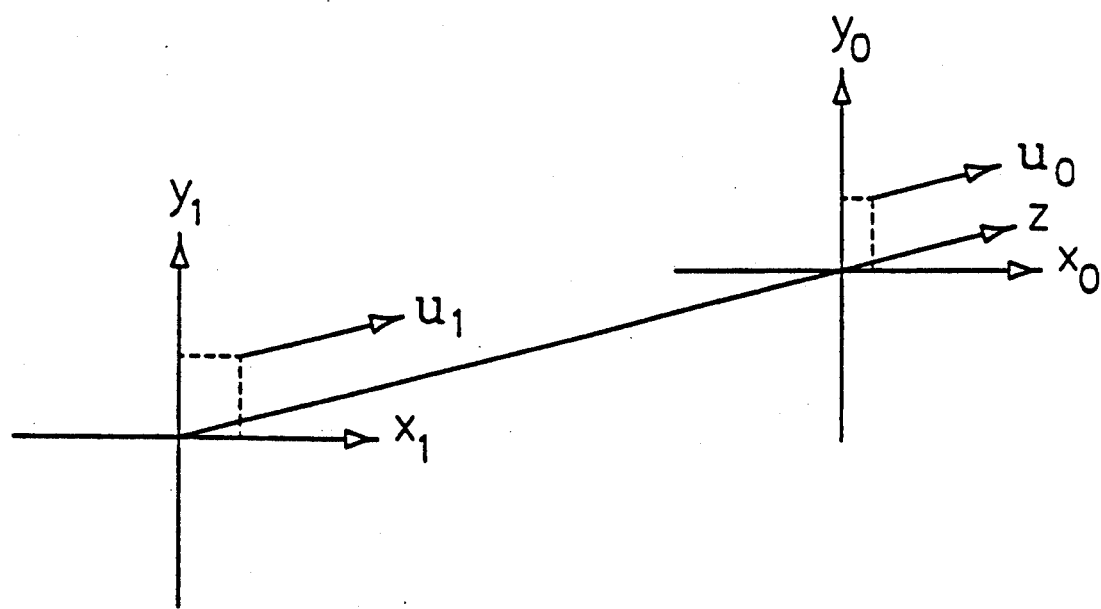

FIG. 3. The phasor $\mu_1$ in the $x_1-y_1$ plane becomes the phasor $u_0$ after propagating a distance z to the $x_0-y_0$ plane.

Figure 4:
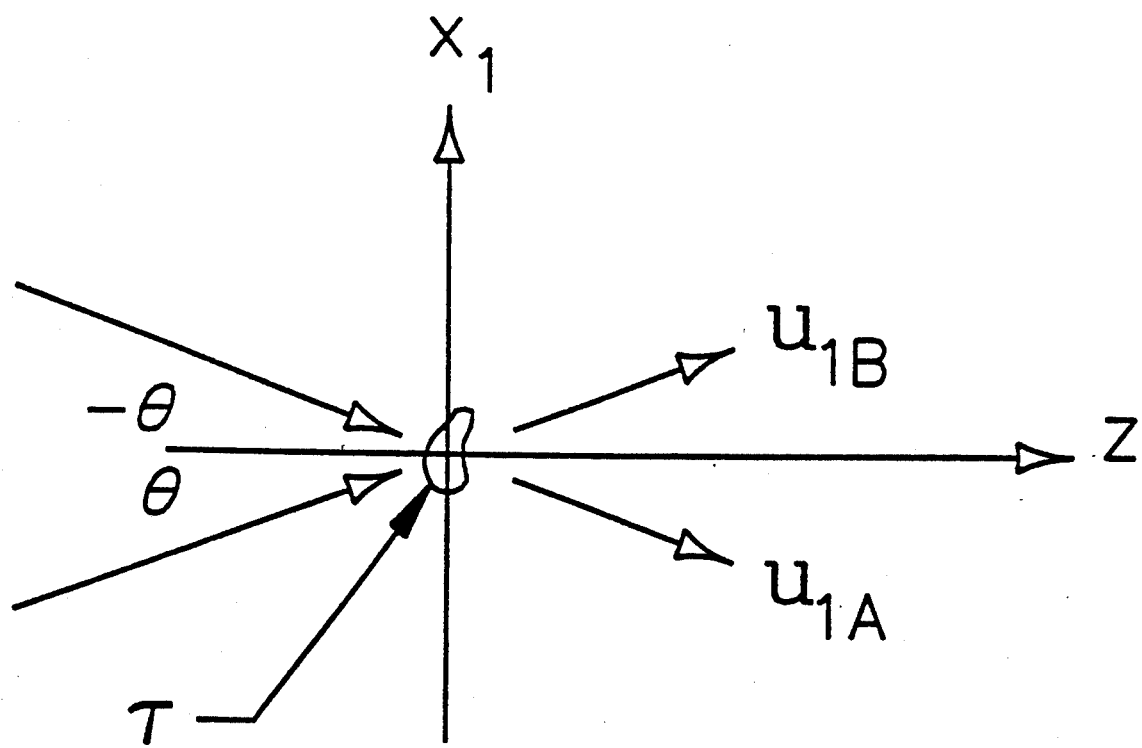

FIG. 4. Symmetric scattering geometry. Two fields propagating in the $x_1-z$ plane at angles $\pm\theta$ from the z-axis intersect at the origin and scatter from an object located there. The transmitted phasors are $\mu_{1A}$ and $\mu_{1B}$.

Figure 5:
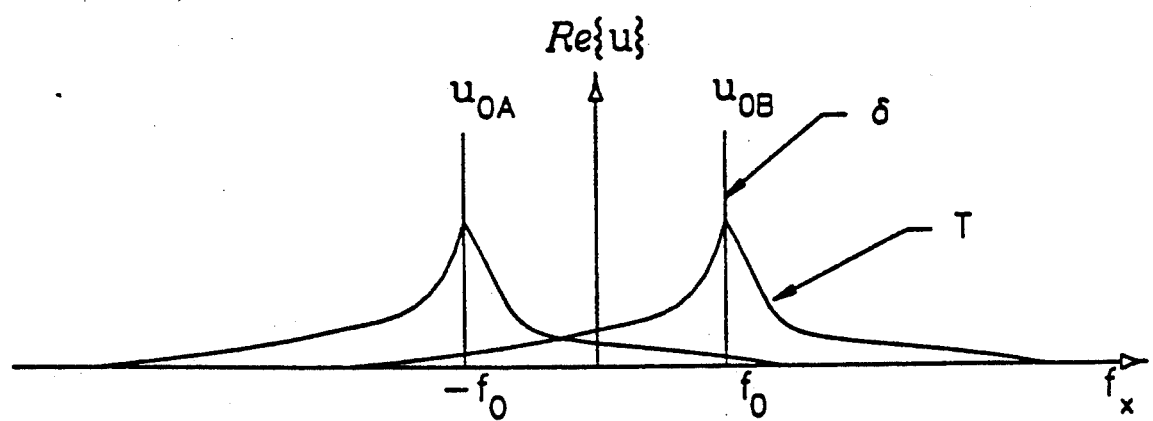

FIG. 5. The real part of the scattered phasors as a function of $f_x=x_0/\lambda z$.

DETAILED DESCRIPTION OF THE PREFERRED EMBODIMENTS

Figure 1:
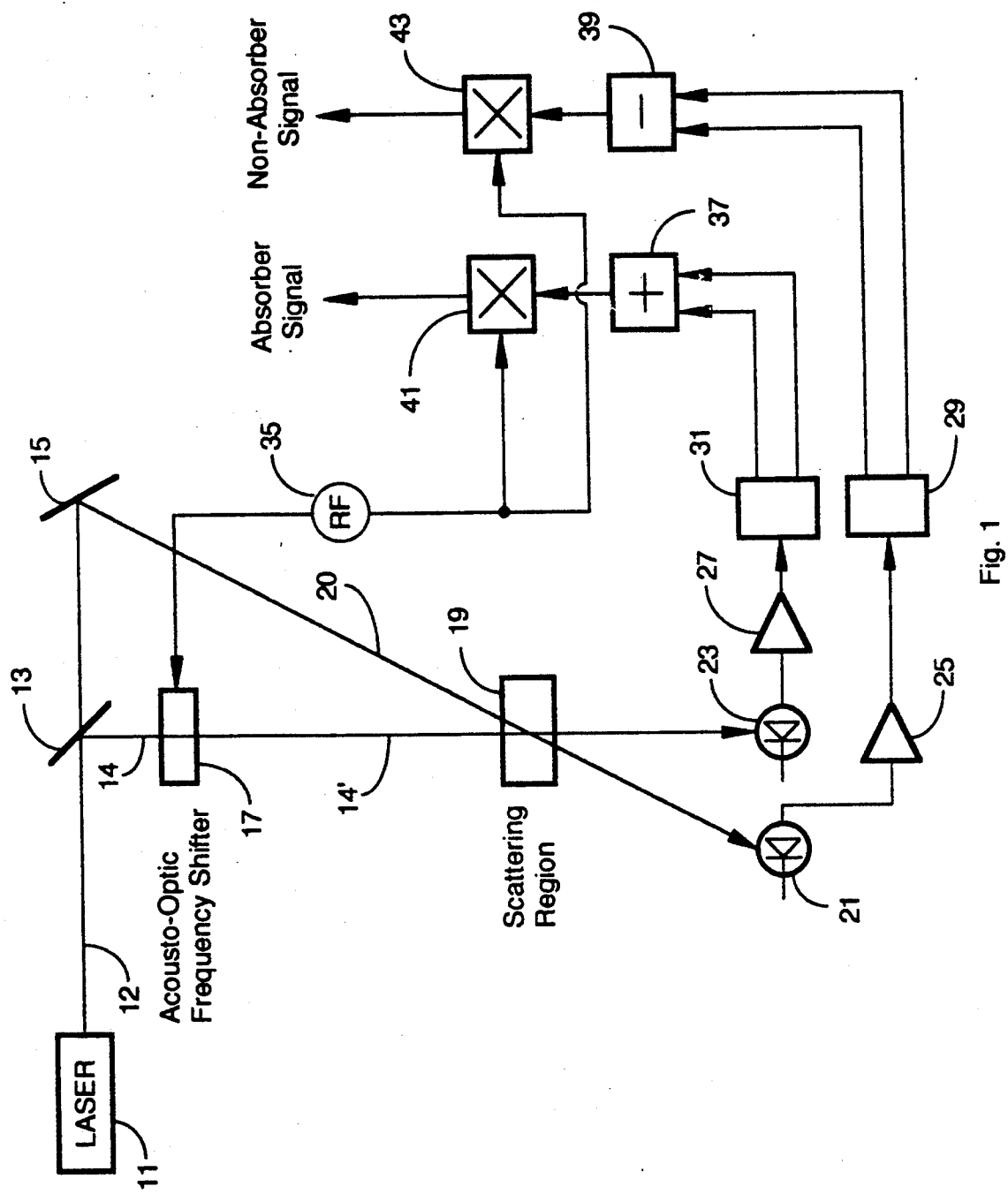
FIG. 1. A schematic representation of a preferred embodiment of the invention.

Shown in FIG. 1 is a laser detection system which can be used to distinguish scattering from absorption in an optical scattering medium, an important process for determining quality of some products. Those skilled in the art will realize that such products could be beverages, optical components, gases, or just about any medium for which scattering (from particulates for example) would provide some indication of quality, or lack thereof.

An incident beam 12 is provided by a laser 11 which impinges on a 50–50 beam splitter 13, thereby creating two beams, 14 and 20. Beam 14 impinges on an acousto-optic frequency shifter 17 that is controlled by an R.F. generator 35 to provide an R.F. frequency shift (typically on the order of 10's of MHz). A frequency shifted beam 14' exits the frequency shifter and enters a scattering region 19. Beam 20 is directed by mirror 15 toward scattering region 19, so that it intersects beam 14 at some arbitrary angle. In the scattering region, light from each beam scatters into the other. After intersecting in the scattering region, the two beam are intercepted by separate high speed photodetectors, 21 and 23, which for example could photodiodes or photomultipliers. Because the two beams 14' and 20 are at different optical frequencies, the mixing of the light generates heterodyne (beat) signals modulated at the difference frequency on each of the photodetectors. The signals from detectors 21 and 23 are then amplified by R.F. amplifiers 25 and 27. (Further, if desired, the R.F. amplifiers can be used to cut off all but the beat frequency.) The signals from the amplifiers are then directed to R.F. splitters 29 and 31, each of which splits the incoming signal equally. One of the signals from splitter 29 is then added to one of the signals from splitter 31 using an in-phase R.F. power combiner 37. Similarly, the other signal from splitter 29 is subtracted from the other signal from splitter 31 using an R.F. power combiner 39.

With the above arrangement, the resulting signal from combiner 37 is proportional to the correlated part of the signals from the two splitters, since the correlated signals add while the anti-correlated signals cancel. Similarly, the resulting signal from combiner 39 corresponds only to the anti-correlated signals. Because the correlated signals are caused by absorption in the scattering region, while the anti-correlated signals are caused by scattering, e.g. by particles that do not absorb, the above arrangement makes it possible to easily distinguish scattering from absorption.

In order to measure the correlated and anti-correlated signals from combiners 37 and 39, it is useful to shift the R.F. and D.C. In the simplest approach, this can be done by multiplying each signal by an R.F. signal from generator 35, as is illustrated in FIG. 1 by multipliers 41 and 43. Another approach would be to use a phase shifter between R.F. generator 35 and each of multipliers 41 and 43. Then one could use a phase sensitive detector to measure the absorber signal from multiplier 41 by adjusting the phase sensitive detector to obtain the maximum signal. One could similarly determine the anti-correlated signal using another phase sensitive detector in the same way on the signal from multiplier 43.

As alluded to earlier, with the above approach, one can distinguish absorption, e.g. due to absorbing particulates, from scattering due to non-absorbing particulates, i.e. transparent moieties. A good example would be bubbles. Hence, one can easily distinguish bubbles, which do not absorb, from absorbing particulates. This is particularly useful in many different industries which require, for example, particulate free liquids.

Appendix A provides a detailed theoretical analysis in support of the above approach.

APPENDIX A

Figure 2:
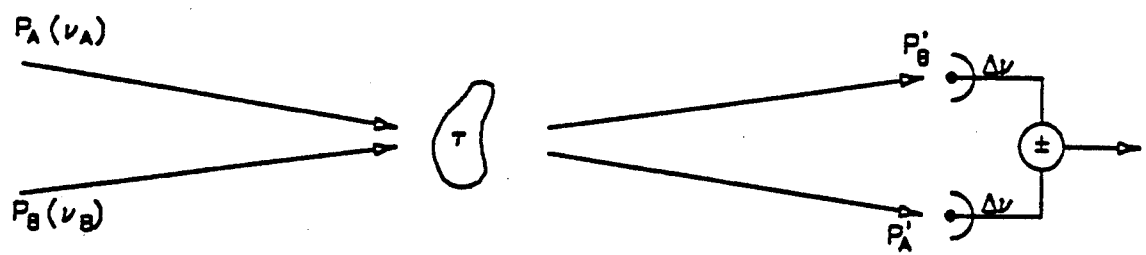

We consider the situation in FIG. 2 in which two laser beams, with correlated optical powers $P_A = P_B = P$, and with optical frequencies differing by an amount $\Delta \nu \equiv \nu_A - \nu_B$, intersect at some point in space. Within the volume of intersection is some arbitrary object that scatters light from each of the two beams into the other beam. We choose the time origin such that at $t=0$ the phase difference of the two beams at the scattering object is zero. After passing through the region containing the scattering object, each of the two beams mixes with some of the scattered light from the other beam on high-quantum-efficiency photodiodes which generate photocurrents proportional to the total power in each of the beams.

The total photocurrent from the two detectors can be written [12]

$$i_A = \rho[(1 - \Sigma_A)P + \sigma_{BA}^2 P + 2\sqrt{(1 - \Sigma_A)P\sigma_{BA}^2 P} \cos(2\pi \Delta \nu t + \phi_A)] \quad (6)$$

$$i_B = \rho[(1 - \Sigma_B)P + \sigma_{AB}^2 P + 2\sqrt{(1 - \Sigma_B)P\sigma_{AB}^2 P} \cos(2\pi \Delta \nu t + \phi_B)], \quad (7)$$

where $$\rho \equiv \eta \epsilon / h\nu \quad (8)$$

is the photodetective responsivity, h is the Planck constant and $\nu$ is the optical frequency. The phase of the heterodyne signal of the ith beam (i = A or B) is $\phi_i$. $\Sigma_i$ is the total fraction of light scatter out of the ith beam, and $\sigma_{ij}$ is the fractional amplitude of the light scattered from the ith beam that mixes with the jth beam to produce a heterodyne signal. If the scattering is weak, such that $\Sigma_i << 1$ then the photocurrents may be written $$i_A(t) \approx \rho P[1 + 2\sigma_{BA} \cos(2\pi \Delta \nu t + \phi_A)] \quad (9)$$

$$i_B(t) \approx \rho P[1 + 2\sigma_{AB} \cos(2\nu \Delta \pi t + \phi_B)] \quad (10)$$

The relationships between the scattering coefficients $\sigma_{BA}$ and $\sigma_{AB}$ and between the ophases $\phi_A$ and $\phi_B$ of the heterodyne signals are found using scalar diffraction theory [13]. For a field propagating along the z-axis, as shown in FIG. 3, the complex phasor $\mu_0$ of an electromagnetic field in the $x_0 - y_0$ plane is found given a known phasor $\mu_1$ in the $x_1 - y_1$ plane, where the two planes are separated by a distance z. In the Fraunhofer approximation.

$$z >> k(x_1^2 + y_1^2)_{max}/2. \quad (11)$$

the complex phasor in the $x_0 - y_0$ plane is given by $$u_0(f_x, f_y) = h \int \int_{-\infty}^{\infty} u_1(x_1 \cdot y_1) \exp[-i2\pi(f_x x_1 + f_y y_1)] dx_1 dy_1 \quad (12)$$
$$= hF\{u_1\},$$

where $f_x = x_0/\lambda z$ and $f_y = y_0/\lambda z$ are the spatial frequencies in the $x_0 y_0$ plane, and $$h = \frac{\exp(ikz)\exp[ik(x_0^2 + y_0^2)/2z]}{ikz}. \quad (13)$$

The symbol F{} indicates the two-dimensional Fourier transform, and bold face implies a complex quantity.

In the symmetric scattering geometry shown in FIG. 4 a weakly scattering object, with complex transmission $\tau$, is centered at the origin of the $x_1 - y_1 - z$ coordinate system. We write the transmission of the object as $$\tau = (1 - \alpha)\exp(i\beta) \quad (14)$$
$$\approx 1 - \alpha + i\beta$$

where $\alpha$, the absorptive part of the transmission and $\beta$, the phase shifting part of the transmission are both real and small compared to one. Without loss of generality, we can decompose both the absorptive and the phase shifting parts of the transmission function into even and odd symmetry functions $$-\alpha = \tau_{RE} + \tau_{RO}$$

$$\beta = \tau_{IE} + \tau_{IO} \tag{15}$$

and re-write Eq. (14) as $$\tau = 1 + \tau_{RE} + \tau_{RO} + i\tau_{IE} + i\tau_{IO} \tag{16}$$

where the subscripts R and I stand for real and imaginary, and the subscripts E and O stand for even and odd symmetry (along the $x_1$-axis).

Two collimated beams with equal amplitudes E propagating in the $x_1-z$ plane along directions $\pm\theta$ with respect to the z-axis intersect at the origin and are scattered by the object. If the object is thin, then the phasors of the fields leaving the $x_1-y_1$ plane are given by $$\mu_{IA} = E\tau \exp(-i2\pi x f_0) \tag{17}$$

$$\mu_{IB} = E\tau \exp(i2\pi x f_0) \tag{18}$$

where $f_0 = \sin\theta/\lambda$. From Eq. (12), the phasors in the $x_0-y_0$ plane are given by $$u_{OA} = EhF\{u_{1A}\} \tag{19}$$
$$= EhT(f_x - f_0)$$

$$u_{OB} = EhT(f_x + f_0) \tag{20}$$

where we have used the Fourier transforms shift thereon, and $$T = F\{\tau\} \tag{21}$$
$$= \delta(f_x) + T_{RE}(f_x) + iT_{IO}(f_x) + iT_{IE}(f_x) + T_{RO}(f_x).$$

Each term in Eq. (21) is the Fourier transform of the corresponding term of Eq. (16): that is $$F\{\tau_{RE}\} = t_{RE}$$

$$R\{\tau_{RO}\} = iT_{IO}$$

$$F\{i\tau_{IE}\} = iT_{IE}$$

$$F\{i\tau_{IO}\} = T_{RO}. \tag{22}$$

The real parts of representative phasors $\mu_{OA}$ and $\mu_{OB}$ are shown in FIG. 5 as a function of the spatial frequency $f_x$. The phasors consist of strong unscattered components at $f_x = \pm f_0$ corresponding to each delta function in Eqs. (19) and (20), and an associated weak scattered component extending over some range from the unscattered component. For the thin scatterer we have assumed, the phasors $\mu$OA and $\mu_{OB}$ are identical except for a displacement along the $f_x$ axis.

The scattered intensity as a function of the spatial frequency, $f_x$, is given by the square magnitude of the field, with the time dependence explicitly included.

$$I(f_x) = |u_{OA}\exp(-i2\pi\nu_A t) + u_{OB}\exp(-i2\pi\nu_B t)|^2 \tag{23}$$
$$= |u_{OA}|^2 + |u_{OB}|^2 + [u_{OA}u_{OB}\exp(-i2\pi > \nu t) + c.c.]$$

where $\Delta\nu - \nu_B$. From Eqs. (19-23), the intensity is written $$I(f_x) \propto E^2|h|^2\{\delta^2(-) + \delta^2(+) + \tag{24}$$
$$2[\delta(-)T_{RE}(+) + \delta(-)T_{RO}(+) +$$
$$\delta(+)T_{RE}(-) + \delta(+)T_{RO}(-)]\cos(2\pi > \nu t) +$$
$$2[\delta(-)T_{IO}(+) + \delta(-)T_{IE}(+) -$$
$$\delta(+)T_{IO}(-) - \delta(+)T_{IE}(-)]\sin(2\pi > \nu t)\}$$

where $(\pm)$ stands for $(f_x \pm f_0)$. In Eq. (24) we have used the relationship $\delta(-)\delta(+) = 0$, and have also neglected terms of second order in the scattering coefficients $T_{XX}$.

The photocurrent generated by a detector is proportional to the total power P incident on the detector surface. For two detectors with responsivity $\rho$ which are located at positions corresponding to $f_x = \pm f_o$, the generated photocurrents are $$i_A(t) = \rho P\{1 + 2[T_{RE}(2f_x) + T_{RO}(2f_x)] \cos(2\pi\Delta\nu t)$$
$$+ 2[T_{IO}(2f_x) + T_{IE}(2F_x)] \sin(2\pi\Delta\nu t)\} \tag{25}$$

$$i_B(t) = \rho P\{1 + 2[T_{RE}(2f_x) - T_{RO}(2f_x)] \cos(2\pi > \nu t) + 2[T_{IO}(2f_x) - T_{IE}(2f_x)] \sin(2\pi\Delta\nu t)\}. \tag{26}$$

We see by comparison with Eqs. (9) and (10) that, for example, $$\sigma_{BA} = \sqrt{(T_{RE} + T_{RO})^2 + (T_{IO} + T_{IE})^2} \tag{27}$$

and $$\phi_A = \tan^{-1}\frac{T_{IO} + T_{IE}}{T_{RE} + T_{RO}}. \tag{28}$$

The photo currents from the two detectors, $i_A$ and $i_B$, can be added or subtracted in external circuitry. From Eqs. (25-26), the sum current is $$i_\Sigma(t) = 2\rho P\{1 + 2T_{RE}(2f_x) \cos(2\pi\Delta\nu t) + 2T_{IO}(2f_x) \sin(2\pi\Delta\nu t)\}. \tag{29}$$

and the difference current is $$i_\Delta(t) = \rho P\{T_{RO}(2f_x) \cos(2\pi\Delta\nu T) + T_{IE}(2f_x) \sin(2\sigma\Delta\nu t)\}. \tag{30}$$

The modulated part of the difference current has a cosine term proportional to $T_{RO}$ and a sine term proportional to $T_{IE}$. From Eqs. (22) and (15), we see that the cosine term is proportional to $\tau_{IO}$ and the sine term is proportional to $\tau$hd IE, and that the difference current is therfore related only to the imaginary part of the scattering function $\tau$. Similarly, the sum current has a cosine term proportional to $\tau_{RE}$ and a sine term proportional to $\tau_{RO}$ and is therefore related only to the real part of the scattering function.

REFERENCES

[1] R. E. Slusher, L. W. Hollberg, B. Yurke, J. C. Mertz, and J. F. Valley, "Observation of squeezed states generated by four-wave mixing in an optical cavity," *Phys. Rev. Lett.* 55(22), 2409-2412 (1985).

[2] L. Wu, H. J. Kimble, J. L. Hall, and H. Wu, "Generation of squeezed states by parametric down conversion." *Phys. Rev. Lett.* 57(20), 2520-2523 (1986).

[3] R. M. Shelby, M. D. Levenson, S. H. Perlmutter, R. G. DeVoe, and D. F. Walls, "Broad-band parametric deamplification of quantum noise in an optical fiber," *Phys. Rev. Lett.*, 57, 691-694 (1986).

[4] S. Machida and Y. Yamamoto, "Ultrabroadband amplitude squeezing in a semiconductor laser," *Phys. Rev. Lett.* 60(9), 792-794 (1988).

[5] A. Heidmann, R. J. Horowicz, S. Reynaud, E. Giacobino, and C. Fabre, "Observation of quantum noise reduction on twin laser beams," *Phys. Rev. Lett.*, 59, 2555-2557 (1987).

[6] M. Xiao, L. Wu, and H. J. Kimble, "Precision measurement beyond the shot-noise limit," *Phys. Rev. Lett.* 59(3), 278-281 (1987).

[7] P. Grangier, R. E. Slusher, B. Yurke, and A. LaPorta, "Squeezed-light-enhanced polarization interferometer," *Phys. Rev. Lett.* 59(19), 2153-2156 (1987).

[8] S. Reynaud, C. Fabre, and E. Giacobino, "Quantum fluctuations in a two-mode parametric oscillator," *J. Opt. Soc. Am. B.* 4, 1320-1524 (1987).

[9] T. Debuisschert, S. Reynaud, A. Heidmann, E. Giacobino, and C. Fabre, "Observation of large quantum noise reduction using an optical parametric oscillator," *Quantum Opt.*, 1, 3-9 (1989).

[10] C. Fabre, E. Giacobino, A. Heidmann, and S. Reynaud, "Noise characteristics of a non-degenerate optical parametric oscillator—Application to quantum noise reduction," *J. Phys. (France)*, 50, 1209-1225 (1989).

[11] J. J. Synder, R. K. Raj, M. Ducloy, and D. Bloch, "High-sensitivity nonlinear spectroscopy using a frequency-offset pump," *Opt. Lett.*, 5(4), 163-165 (1980).

[12] J. J. Snyder, "Coherent heterodyne radiometry for quantum limited, wide dynamic range optical power measurement," *Appl. Opt.*, 27, 4465-4469 (1988).

What is claimed is:

1. Apparatus for measuring non-absorptive scattering from a scattering region comprising:
   source means for producing two laser beams having equal optical powers, with one of said beams being shifted in frequency relative to the other, said two beams oriented to cross in the scattering region;
   detector means for independently detecting each of said two beams after they have traversed the scattering region, said detector means providing first and second signals, one for each of said two beams;
   differencing means for providing a difference signal proportional to the difference between said first and second signals from said detector means, said difference signal corresponding to the anti-correlated portions of said first and second signals from said detector means.

2. Apparatus as in claim 1 wherein said source means comprises laser means for providing a laser beam, splitter means for slitting said laser beam into said two beams, shifter means for shifting the frequency of one of said two beams relative to the other, and means for directing said two beams to cross in the scattering region.

3. Apparatus as in claim 2 wherein said differencing means comprises first amplifier means for amplifying said first signal, first splitter means for splitting said first amplified signal into two equal first splitter signals, second amplifier means for amplifying said second signal, and second splitter means for splitting said second amplified signal into two equal second splitter signals, and combiner means for subtracting one of said first splitter signals from one of said second splitter signals.

4. Apparatus as in claim 1 wherein said detector means comprises first and second separate photodetectors, one for each of said two beams, said first photodetector providing said first signal and said second photodetector providing said second signal.

5. Apparatus as in claim 1 wherein said differencing means comprises multiplier means for multiplying said difference signal by an R.F. signal to shift said difference signal to D.C.

6. Apparatus as in claim 1 further comprising summing means for providing a sum signal proportional to the sum of said first and second signals from said detector means, said sum signal corresponding to the correlated portions of said first and second signals from said detector means.

7. Apparatus for measuring absorptive scattering from a scattering region comprising:
   source means for producing two laser beams having equal optical powers, with one of said beams being shifted in frequency relative to the other, said two beams oriented to cross in the scattering region;
   detector means for independently detecting each of said two beams after they have traversed the scattering region, said detector means providing first and second signals, one for each of said two beams;
   summing means for providing a sum signal proportional to the sum of said first and second signals from said detector means, said sum signals corresponding to the correlated portions of said first and second signals from said detector means.

* * * * *